United States Patent [19]
Hicks et al.

[11] Patent Number: 5,545,705
[45] Date of Patent: Aug. 13, 1996

[54] ALDIMINES BASED ON 2-METHYL-1,5-PENTANE DIAMINE AND THEIR USE FOR THE PRODUCTION OF POLYUREA COATINGS

[75] Inventors: Sharon D. Hicks, Pittsburgh; Douglas A. Wicks, Mt. Lebanon; Scott A. Grace, Coraopolis, all of Pa.

[73] Assignee: Bayer Corporation, Pittsburgh, Pa.

[21] Appl. No.: 355,590

[22] Filed: Dec. 14, 1994

[51] Int. Cl.$^6$ .................. C08G 18/00; C07C 249/00; C07C 251/00; C09K 3/00
[52] U.S. Cl. .................. 528/44; 106/287.2; 106/287.25; 252/182.2; 252/182.13; 564/248; 564/271; 564/272; 564/278; 528/52; 528/73
[58] Field of Search .................. 528/44, 73, 52; 106/287.2, 287.25; 252/182.2, 182.13; 564/248, 278, 272, 271

[56] References Cited

U.S. PATENT DOCUMENTS

| | | | |
|---|---|---|---|
| 3,420,800 | 1/1969 | Haggis | 260/75 |
| 3,567,692 | 3/1971 | Haggis | 260/75 |
| 4,820,830 | 4/1989 | Blank | 528/370 |
| 5,026,147 | 6/1991 | Soane et al. | 350/374 |
| 5,142,013 | 8/1992 | Cassidy et al. | 528/44 |

OTHER PUBLICATIONS

Odian, Principles of Polymerization, 1981, pp. 28–29.

*Primary Examiner*—Paul R. Michl
*Assistant Examiner*—Patrick Niland
*Attorney, Agent, or Firm*—Joseph C. Gil; Thomas W. Roy

[57] ABSTRACT

The present invention relates to aldimines corresponding to the formula

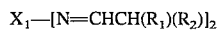

$$X_1\text{—}[N\text{=}CHCH(R_1)(R_2)]_2$$

wherein
  $X_1$ represents the group obtained by the removal of the amino groups from 2-methyl-1,5-pentane diamine,
  $R_1$ and $R_2$ may be the same or different and represent optionally substituted hydrocarbon radicals, or $R_1$ and $R_2$ together with the β-carbon atom from a cycloaliphatic or heterocyclic ring.

The present invention relates to a clear, solvent-containing coating composition which contains
  a) an isocyanurate group-containing polyisocyanate which contains less than 5% by weight, based on the weight of component a), of allophanate and uretdione groups and
  b) an aldimine corresponding to the formula

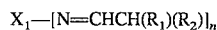

$$X_1\text{—}[N\text{=}CHCH(R_1)(R_2)]_n$$

wherein $X_1$, $R_1$ and $R_2$ are as previously defined and
  c) 10 to 200% by weight, based on the weight of components a), b) and c), of a organic solvent containing only ester groups,
wherein components a) and b) are present in an amount sufficient to provide an equivalent ratio of isocyanate groups to aldimine groups of 0.5:1 to 20:1.

15 Claims, No Drawings

ALDIMINES BASED ON 2-METHYL-1,5-PENTANE DIAMINE AND THEIR USE FOR THE PRODUCTION OF POLYUREA COATINGS

BACKGROUND OF THE INVENTION

1. Field of the Invention

The present invention relates to aldimines based on 2-methyl-1,5-pentane diamine and their use in combination with isocyanurate group-containing polyisocyanates as binder components for the production of coatings with improved optical properties, e.g., clarity.

2. Description of the Prior Art

One-component coating compositions which may be cured at room temperature are known and contain fully reacted polyurethanes as the binder. These compositions have the advantage that they are available as fully formulated systems which may be directly applied to suitable substrates without any preliminary steps except for mild stirring. Disadvantages of these systems are that large amounts of organic solvents are needed to reduce the viscosity of fully reacted, high molecular weight polyurethanes. In addition, the polyurethanes must be essentially linear polyurethanes and, thus, do not possess certain properties, e.g., solvent resistance, which may be obtained from crosslinked polyurethanes.

Two-component coating compositions are also known. These compositions come in two containers. The first contains a polyisocyanate, while the second contains an isocyanate-reactive component, generally a polyol. These systems do not require large amounts of solvent to obtain a suitable processing viscosity and can be used to obtain highly crosslinked coatings which possess properties that surpass those possessed by one-component coatings. However, these systems must be accurately mixed or the properties of the resulting coatings can be substantially affected. In addition, after the components are mixed they have a limited pot life since the components continue to react until an unusable solid is obtained.

Coating compositions which possess the advantages of the known one- and two-component coating compositions without possessing their disadvantages have been disclosed in copending applications, U.S. Ser. Nos. 08/171,281; 08/171,550; 08/171,304; 08/193,978; 08/194,296; 08/273,551; and 08/297,357. The coating compositions are prepared by blending polyisocyanates with certain aldimines and other ingredients depending upon the particular application. Even though coatings prepared in accordance with these copending applications possess many desirable properties, further improvements are needed in the appearance of the coatings, i.e., clarity, gloss and distinctness of image (DOI). These properties are directly related to the compatibility between the polyisocyanate and the aldimine.

Copending application, U.S. Ser. No. 08/171,281, discloses that the compatibility with aldimines may be improved by using certain allophanate group-containing polyisocyanates. However, there is still a need to achieve these improvements in compatibility and appearance with other commercially available polyisocyanates. Copending application, U.S. Ser. No. 08/273,551, discloses that the compatibility of these other commercially available polyisocyanates with aldimines can be improved by incorporating an additional component into the composition. However, the presence of this component reduces the pot life of the coating composition.

It is an object of the present invention to improve the compatibility between polyisocyanates and aldimines so that the clarity, gloss and DOI of the resulting coatings is also improved without the need for special polyisocyanates or the need to incorporate additional ingredients the polyisocyanates with the aldimines.

This object may be achieved with by using aldimines based on 2-methyl-1,5-pentane diamine in combination with isocyanurate group-containing polyisocyanates to prepare coating compositions as described hereinafter.

U.S. Pat. Nos. 3,420,800 and 3,567,692 disclose coating compositions containing polyisocyanates and either aldimines or ketimines. However, these patents do not teach that the compatibility of polyisocyanates with aldimines can be improved by the use of aldimines based on 2-methyl-1,5-pentane diamine.

SUMMARY OF THE INVENTION

The present invention relates to aldimines corresponding to the formula

wherein $X_1$ represents the group obtained by the removal of the amino groups from 2-methyl-1,5-pentane diamine, $R_1$ and $R_2$ may be the same or different and represent optionally substituted hydrocarbon radicals, or $R_1$ and $R_2$ together with the β-carbon atom from a cycloaliphatic or heterocyclic ring.

The present invention relates to a clear, solvent-containing coating composition which contains a) an isocyanurate group-containing polyisocyanate which contains less than 5% by weight, based on the weight of component a), of allophanate and uretdione groups and b) an aldimine corresponding to the formula

wherein $X_1$, $R_1$ and $R_2$ are as previously defined and c) 10 to 200% by weight, based on the weight of components a), b) and c), of a organic solvent containing only ester groups, wherein components a) and b) are present in an amount sufficient to provide an equivalent ratio of isocyanate groups to aldimine groups of 0.5:1 to 20:1.

DETAILED DESCRIPTION OF THE INVENTION

Aldimines in accordance with the present invention are those prepared from 2-methyl-1,5-pentane diamine and an aldehyde corresponding to the formula

wherein $R_1$ and $R_2$ may be the same or different and represent optionally substituted hydrocarbon radicals, preferably containing 1 to 10, more preferably 1 to 6, carbon atoms, or $R_1$ and $R_2$ together with the β-carbon atom form a cycloaliphatic or heterocyclic ring.

Examples of suitable aldehydes include isobutyraldehyde, 2-ethyl hexanal, 2-methyl butyraldehyde, 2-ethyl butyraldehyde, 2-methyl valeraldehyde, 2,3-dimethyl valeraldehyde, 2-methyl undecanal and cyclohexane carboxyaldehyde. Isobutyraldehyde is especially preferred.

The aldimines may be prepared in known manner by reacting the diamine with the aldehydes either in stoichiometric amounts or with an excess of aldehyde. The excess aldehyde and the water which is produced can be removed by distillation. The reactions may also be carried out in solvents other than ketones. The solvents may also be removed by distillation after completion of the reaction.

The aldimines are useful in combination with isocyanurate group-containing polyisocyanates as a binder component in coating compositions for the production of polyurea coatings. In accordance with the present invention the term "polyurea" means polymers exclusively containing urea groups as the isocyanate addition product and also mixtures of urea groups with other isocyanate addition products such as urethane groups.

Examples of suitable polyisocyanates which may be used as the polyisocyanate component in accordance with the present invention are isocyanurate group-containing polyisocyanates. These polyisocyanates have an average functionality of 2.5 to 6, preferably 3 to 3.5, and an NCO content of 5 to 30%, preferably 10 to 25% and more preferably 15 to 25% by weight. The polyisocyanates generally contain less than 5% by weight, preferably less than 3% by weight, based on the weight of the polyisocyanate component, of allophanate and uretdione groups.

The isocyanurate group-containing polyisocyanates may be prepared in known manner by trimerizing a portion of the isocyanate groups of an organic diisocyanate in the presence of a trimerization catalyst, then terminating the reaction at the desired NCO content, e.g., by the addition of a catalyst poison, and optionally removing unreacted diisocyanate starting material, e.g., by distillation. Methods for preparing the isocyanurate group-containing polyisocyanates are described in DE-PS 2,616,416, EP-OS 3,765, EP-OS 10,589, EP-OS 47,452, U.S. Pat. No. 4,288,586 and U.S. Pat. No. 4,324,879.

Suitable monomeric diisocyanates which may be used as starting materials include those represented by the formula

in which R represents an organic group obtained by removing the isocyanate groups from an organic diisocyanate having a molecular weight of about 112 to 1,000, preferably about 140 to 400. Diisocyanates preferred for the process according to the invention are those represented by the above formula in which R represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, α,α, α',α'-tetramethyl-1,3- and/or -1,4-xylylene diisocyanate, 1-isocyanato-1-methyl-4(3 )-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4and/or 4,4'-diphenyl-methane diisocyanate, 1,5-diisocyanato naphthalene and mixtures thereof. Aromatic polyisocyanates containing 3 or more isocyanate groups such as 4,4',4"-triphenylmethane diisocyanate and polyphenyl polymethylene polyisocyanates obtained by phosgenating aniline/formaldehyde condensates may also be used.

Preferred starting diisocyanates for preparing the isocyanurate group-containing polyisocyanates are 1,6-hexamethylene diisocyanate and isophorone diisocyanate. 1,6-hexamethylene diisocyanate is especially preferred.

The isocyanurate group-containing polyisocyanates may be blended with the aldimines according to the invention in the presence of organic solvents that only contain ester groups, such as butyl acetate, to form clear binders that are suitable to prepare clear top coats, e.g., for automotive clearcoat applications. As demonstrated in the examples of the subject application, aldimines prepared from other diamines do not result in clear binders in the presence of butyl acetate.

The binder components are used in amounts sufficient to provide an equivalent ratio of isocyanate groups to aldimine groups of 0.5:1 to 20:1, preferably 0.8:1 to 3:1 and more preferably 1:1 to 2:1. The binders according to the invention are prepared by simply mixing the individual components together. Preparation of the binder mixtures is carried out solvent-free or in the presence of the solvents conventionally used in polyurethane or polyurea coatings. It is an advantage of the present invention that the quantity of solvent used may be greatly reduced when compared with that required in conventional two-component systems based on polyisocyanates and polyols.

The coating compositions according to the invention contain 10 to 200%, preferably 25 to 150%, based on the weight of binder solids, of ester group-containing organic solvents.

In addition to the binder components and solvents, the coating compositions may also contain the known additives from coatings technology, such as fillers, pigments, softeners, high-boiling liquids, catalysts, UV stabilizers, antioxidants, microbiocides, algicides, dehydrators, thixotropic agents, wetting agents, flow enhancers, matting agents, anti-slip agents, aerators and extenders. Coating compositions containing pigments and/or fillers are especially suitable for the present invention due to the difficulty of removing all of the moisture from these additives.

It is also possible to incorporate other additives which increase the pot life of compositions containing polyisocyanates and aldimines, such as the tin compounds disclosed in copending application, U.S. Ser. No. 08/171,304, herein incorporated by reference; or the zeolites disclosed in copending application, U.S. Ser. No. 08/193,978, herein incorporated by reference.

The additives are chosen based on the requirements of the particular application and their compatibility with the binder components. The coating compositions may be applied to the substrate to be coated by conventional methods such as painting, rolling, pouring or spraying. It is especially advantageous to apply the coating compositions by spraying since they may be diluted to a suitable spray viscosity of less than 100 mPa•s, preferably less than 60 mPa•s, without the need for large amounts of solvent.

The coating compositions according to the invention have good storage stability and provide coatings which have relatively fast dry times. The coatings are also characterized by high hardness, elasticity, very good resistance to chemicals, high gloss, good weather resistance, good environmental etch resistance and good pigmenting qualities.

The invention is further illustrated, but is not intended to be limited by the following examples in which all parts and percentages are by weight unless otherwise specified.

EXAMPLES

The following starting materials were used in the examples:

Polyisocyanate 1

An isocyanurate group-containing polyisocyanate present as a 90% solution in a 1:1 blend of butyl acetate and aromatic 100, prepared from 1,6-hexamethylene diisocyanate and having an isocyanate content of 19.4%, based on solution, a content of monomeric diisocyanate of <0.15% and a viscosity at 25° C. of about 500 mPa·s (available from Miles Inc. as Desmodur N 3390).

Aldimine 1

116 parts of 2-methyl-1,5-pentane diamine (1.0 mole) were charged at ambient temperature into a three necked 500 ml flask equipped with a mechanical stiffer, thermometer, and an addition funnel. 158.4 parts of isobutyraldehyde (2.2 mole) were added dropwise via the addition funnel to the stirred contents of the flask at a rate such that the exotherm of the reaction did not increase the temperature of the reaction mixture above 50° C. During the course of the reaction water was generated as a by-product as evidenced by the gradual change in the appearance of the reaction contents to a milky white mixture. Upon complete addition of the aldehyde, the reaction mixture was heated to maintain a temperature of 50° C. for a period of 1 hour. The water (36 g; 2.0 moles) and excess isobutyraldehyde were removed by azeotropic distillation, followed by a vacuum (ca. 1 torr) stripping step to remove trace quantities of water. The finished product was a clear, almost colorless (<100 APHA) liquid having a viscosity of about 10 mPa·s (25° C.) and an equivalent weight of 112 g/eq.

Aldimine 2

The aldimine of 1,6-hexamethylene diamine and isobutryaldehyde was prepared using the procedure set forth for Aldimine 1. The finished product was a clear, almost colorless (<100 APHA) liquid having a viscosity of about 10 mPa·s (25° C.) and an equivalent weight of 112 g/eq.

Aldimine 3

The aldimine of 1,3-pentane diamine and isobutryaldehyde was prepared using the procedure set forth for Aldimine 1. The finished product was a clear, almost colorless (<100 APHA) liquid having a viscosity of about 10 mPa·s (25° C.) and an equivalent weight of 105 g/eq.

Preparation of Improved Compatibility Amine Co-Reactants: According to the Invention:

Examples 1–3

The aldimines and polyisocyanate set forth in the following table were blended at an NCO/NH equivalent ratio of 1.1:1.0. The reactive components were blended with 0.5%, based on resin solids, of a flow control aid (a polyacrylate copolymer, available as Byk 358 from Byk Chemie) and sufficient butyl acetate to form 65% solids compositions. The appearance of the coating compositions was evaluated after mixing and also after about 24 hrs. Ratings were assigned based on the following scale:

| Liquid Appearance: | 0 - clear solution |
| | 1 - very slight haze |
| | 2 - slight haze |
| | 3 - haze |
| | 4 - gel particles present |

| FORMULATION | EXAMPLE NO. | | |
| | 1 | 2 (Comp) | 3 (Comp) |
| --- | --- | --- | --- |
| Aldimine 1 | 22.2 | | |
| Aldimine 2 | | 22.2 | |
| Aldimine 3 | | | 21.3 |
| Polyiso 1 | 47.2 | 47.2 | 48.2 |
| Flow Control Additive | 0.6 | 0.6 | 0.6 |
| Butyl Acetate | 30 | 30 | 29.9 |
| Appearance | 0 | 2/3 | 4 |

The results set forth in the preceding table demonstrate the unexpected compatibility of isocyanurate group-containing polyisocyanates with the aldimines according to the invention, which are based on 2-methyl-1,5-pentane diamine, when compared to structurally similar aldimines based on 1,6-hexamethylene diamine and 1,3-pentane diamine.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An aldimine corresponding to the formula $$X_1-[N=CHCH(R_1)(R_2)]_2$$

wherein $X_1$ represents the group obtained by the removal of the amino groups from 2-methyl-1,5-pentane diamine, $R_1$ and $R_2$ may be the same or different and represent hydrocarbon radicals, or $R_1$ and $R_2$ together with the β-carbon atom from a cycloaliphatic or heterocyclic ring.

2. The aldimine of claim 1 wherein $R_1$ and $R_2$ are hydrocarbon radicals containing 1 to 6 carbon atoms.

3. The aldimine of claim 1 wherein $R_1$ is methyl and $R_2$ is ethyl.

4. A clear, solvent-containing coating composition comprising a) an isocyanurate group-containing polyisocyanate which contains less than 5% by weight, based on the weight of component a), of allophanate and uretdione groups and b) an aldimine corresponding to the formula $$X_1-[N=CHCH(R_1)(R_2)]_n$$

wherein $X_1$ represents the group obtained by the removal of the amino groups from 2-methyl-1,5-pentane diamine, $R_1$ and $R_2$ may be the same or different and represent hydrocarbon radicals, or $R_1$ and $R_2$ together with the β-carbon atom form a cycloaliphatic or heterocyclic ring, and c) 10 to 200% by weight, based on the weight of components a), b) and c), of a organic solvent containing only ester groups, wherein components a) and b) are present in an amount sufficient to provide an equivalent ratio of isocyanate groups to aldimine groups of 0.5:1 to 20:1.

5. The coating composition of claim 4 wherein $R_1$ and $R_2$ are hydrocarbon radicals containing 1 to 6 carbon atoms.

6. The coating composition of claim 4 wherein $R_1$ is methyl and $R_2$ is ethyl.

7. The coating composition of claim 4 wherein said isocyanurate group-containing polyisocyanate is based on 1,6-hexamethylene diisocyanate.

8. The coating composition of claim 5 wherein said isocyanurate group-containing polyisocyanate is based on 1,6-hexamethylene diisocyanate.

9. The coating composition of claim 6 wherein said isocyanurate group-containing polyisocyanate is based on 1,6-hexamethylene diisocyanate.

10. A clear, solvent-containing coating composition comprising
    a) an isocyanurate group-containing polyisocyanate which contains less than 5% by weight, based on the weight of component a), of allophanate and uretdione groups and
    b) an aldimine corresponding to the formula $$X_1\text{—}[N\!=\!CHCH(R_1)(R_2)]_n$$

wherein $X_1$ represents the group obtained by the removal of the amino groups from 2-methyl-1,5-pentane diamine, $R_1$ and $R_2$ may be the same or different and represent hydrocarbon radicals, or $R_1$ and $R_2$ together with the β-carbon atom form a cycloaliphatic or heterocyclic ring, and c) 10 to 200% by weight, based on the weight of components a), b) and c), of butyl acetate, wherein components a) and b) are present in an amount sufficient to provide an equivalent ratio of isocyanate groups to aldimine groups of 0.5:1 to 20:1.

11. The coating composition of claim 10 wherein $R_1$ and $R_2$ are hydrocarbon radicals containing 1 to 6 carbon atoms.

12. The coating composition of claim 10 wherein $R_1$ is methyl and $R_2$ is ethyl.

13. The coating composition of claim 10 wherein said isocyanurate group-containing polyisocyanate is based on 1,6-hexamethylene diisocyanate.

14. The coating composition of claim 11 wherein said isocyanurate group-containing polyisocyanate is based on 1,6-hexamethylene diisocyanate.

15. The coating composition of claim 12 wherein said isocyanurate group-containing polyisocyanate is based on 1,6-hexamethylene diisocyanate.

* * * * *